(12) United States Patent
Legrand

(10) Patent No.: US 7,691,841 B2
(45) Date of Patent: Apr. 6, 2010

(54) AZETIDINE DERIVATIVES AS CCR-3 RECEPTOR ANTAGONIST

(75) Inventor: Darren M Legrand, Horsham (GB)

(73) Assignee: Novartis AG, Basel (CH)

( * ) Notice: Subject to any disclaimer, the term of this patent is extended or adjusted under 35 U.S.C. 154(b) by 112 days.

(21) Appl. No.: 11/573,232

(22) PCT Filed: Aug. 9, 2005

(86) PCT No.: PCT/EP2005/008654

§ 371 (c)(1),
(2), (4) Date: Feb. 5, 2007

(87) PCT Pub. No.: WO2006/015854

PCT Pub. Date: Feb. 16, 2006

(65) Prior Publication Data

US 2007/0259848 A1 Nov. 8, 2007

(30) Foreign Application Priority Data

Aug. 10, 2004 (GB) .................. 0417801.8

(51) Int. Cl.
| | | |
|---|---|---|
| A61K 31/397 | (2006.01) | |
| A61P 29/00 | (2006.01) | |
| A61P 37/00 | (2006.01) | |
| C07D 205/04 | (2006.01) | |
| C07D 277/62 | (2006.01) | |
| C07D 401/14 | (2006.01) | |
| C07D 403/02 | (2006.01) | |
| C07D 413/02 | (2006.01) | |

(52) U.S. Cl. .................. 514/210.01; 548/950; 548/156; 548/373.1; 548/215; 546/193; 546/276.4

(58) Field of Classification Search ............. 514/210.01
See application file for complete search history.

(56) References Cited

U.S. PATENT DOCUMENTS

| | | | | |
|---|---|---|---|---|
| 7,288,537 B2 * | 10/2007 | Le Grand et al. | ....... | 514/210.01 |
| 2006/0252751 A1 * | 11/2006 | Xue et al. | ......... | 514/235.2 |
| 2007/0043013 A1 * | 2/2007 | Le Grand | ............ | 514/210.01 |

FOREIGN PATENT DOCUMENTS

| | | |
|---|---|---|
| WO | 97/42189 A1 | 11/1997 |
| WO | 03/007939 A1 | 1/2003 |
| WO | 03/077907 | 9/2003 |

OTHER PUBLICATIONS

Goodman, Chamistry and industry, published Mar. 21, 2005.*
Butler et al., Chem Commun, 2003, 1016-1017.*

* cited by examiner

*Primary Examiner*—Brian-Yong S Kwon
*Assistant Examiner*—Bong-Sook Baek
(74) *Attorney, Agent, or Firm*—John Alexander

(57) ABSTRACT

Compounds of formula I

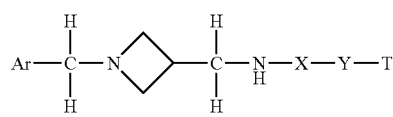

in free or salt form, wherein Ar, X, Y and T have the meanings as indicated in the specification, are useful for treating a condition mediated by CCR-3, particularly an inflammatory or allergic condition such as an inflammatory or obstructive airways disease.

Pharmaceutical compositions that contain the compounds and processes for preparing the compounds are also described.

6 Claims, No Drawings

AZETIDINE DERIVATIVES AS CCR-3 RECEPTOR ANTAGONIST

This invention relates to organic compounds, their preparation and use as pharmaceuticals.

In one aspect, the invention provides compounds of formula I

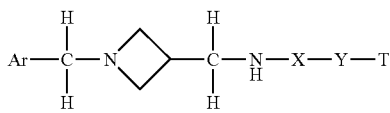

in free or salt form, wherein

Ar is phenyl optionally substituted by halo, $C_1$-$C_8$-alkyl, $C_1$-$C_8$-alkoxy, cyano, nitro, —$SO_2$—$C_1$-$C_8$-alkyl, —$SO_2$—NH—$C_1$-$C_8$-alkyl and —$SO_2$—N—$(C_1$-$C_8$-alkyl$)_2$;

X is a bond or —CO—$CH_2$—NH—;

Y is —CO—$R^1$—, —CO—$R^2$—S—, —CO—NH— or —$SO_2$—;

T is a cyclic group selected from $C_1$-$C_8$-cycloalkyl, phenyl optionally substituted by halo, $C_1$-$C_8$-alkyl, $C_1$-$C_8$-alkoxy or cyano, and a heterocyclic group having 5 to 10 ring atoms wherein at least one of those ring atoms is a nitrogen, oxygen or sulphur atom, said heterocyclic group being optionally substituted by halo, $C_1$-$C_8$-alkyl optionally substituted by $R^3$, $C_1$-$C_8$-alkoxy optionally substituted by $R^3$, phenyl or by a 5- or 6-membered heterocyclic ring having at least one ring nitrogen, oxygen or sulphur atom;

$R^1$ and $R^2$ are each a bond or $C_1$-$C_8$-alkylene; and $R^3$ is phenyl or a 5- or 6-membered heterocyclic ring having at least one ring nitrogen, oxygen or sulphur atom.

Terms used in the specification have the following meanings:

"$C_1$-$C_8$-alkyl" as used herein denotes straight chain or branched alkyl having one to eight carbon atoms. Preferably $C_1$-$C_8$-alkyl is $C_1$-$C_4$-alkyl.

"$C_1$-$C_8$-alkylene" as used herein denotes a straight chain or branched alkylene that contains one to eight carbon atoms. Preferably $C_1$-$C_{10}$-alkylene is $C_1$-$C_4$-alkylene, especially methylene.

"$C_1$-$C_8$-alkoxy" as used herein denotes straight chain or branched alkoxy having one to eight carbon atoms. Preferably $C_1$-$C_8$-alkoxy is $C_1$-$C_4$-alkoxy.

"$C_3$-$C_8$-cycloalkyl" denotes cycloalkyl having 3 to 8 ring carbon atoms, for example a monocyclic group such as a cyclopropyl, cyclobutyl, cyclopentyl, cyclohexyl, cycloheptyl or cyclooctyl, any of which can be substituted by one or more, usually one or two, $C_1$-$C_4$-alkyl groups, or a bicyclic group such as bicycloheptyl or bicyclooctyl. Preferably "$C_3$-$C_8$-cycloalkyl" is cyclopropyl, cyclobutyl, cyclopentyl, cyclohexyl, cycloheptyl or cyclooctyl.

"Halo" or "halogen" as used herein denotes a element belonging to group 17 (formerly group VII) of the Periodic Table of Elements, which may be, for example, fluorine, chlorine, bromine or iodine. Preferably halo/halogen is fluorine, chlorine or bromine.

"Heterocyclic group having 5 to 10 ring atoms wherein at least one of those ring atoms is a nitrogen, oxygen or sulphur atom" as used herein may be, for example, pyrrole, pyrazole, imidazole, triazole, tetrazole, thiadiazole, oxazole, isoxazole, thiazole, isothiazole, benzothiazole oxadiazole, pyridine, oxazole, pyrazine, pyridazine, pyrimidine, piperazine, morpholino, triazine or oxazine. Preferred heterocyclic groups include benzothiazole, pyrrole, oxazole, pyrazole and pyridine.

"5- or 6-membered heterocyclic ring having at least one ring nitrogen, oxygen or sulphur atom" as used herein may be, for example, pyrrole, pyrazole, imidazole, triazole, tetrazole, thiadiazole, oxazole, isoxazole, isothiazole, oxadiazole, pyridine, oxazole, pyrazine, pyridazine, pyrimidine, piperazine, morpholino, triazine, oxazine or thiazole. Preferred heterocyclic rings include pyridine and morpholino.

"Optionally substituted" means the group referred to can be substituted at one or more positions by any one or any combination of the radicals listed thereafter.

Throughout this specification and in the claims that follow, unless the context requires otherwise, the word "comprise", or variations such as "comprises" or "comprising", will be understood to imply the inclusion of a stated integer or step or group of integers or steps but not the exclusion of any other integer or step or group of integers or steps.

Preferred compounds of formula I in free or salt form include those in which

Ar is phenyl optionally substituted by halo;

X is a bond or —CO—$CH_2$—NH—;

Y is —CO—$R^1$—, —CO—$R^2$—S—, —CO—NH— or —$SO_2$—;

T is phenyl optionally substituted by halo, $C_1$-$C_8$-alkyl, $C_1$-$C_8$-alkoxy or cyano, or T is a heterocyclic group having 5 to 10 ring atoms wherein at least one of those ring atoms is a nitrogen, oxygen or sulphur atom, said heterocyclic group being optionally substituted by $C_1$-$C_8$-alkyl optionally substituted by $R^3$, $C_1$-$C_8$-alkoxy, phenyl or by a 5- or 6-membered heterocyclic ring having at least one ring nitrogen, oxygen or sulphur atom;

$R^1$ and $R^2$ are each a bond or $C_1$-$C_8$-alkylene; and $R^3$ is phenyl or a 5- or 6-membered heterocyclic ring having at least one ring nitrogen, oxygen or sulphur atom.

Further preferred compounds of formula I in free or salt form include those in which Ar is phenyl optionally substituted by halo;

X is a bond or —CO—$CH_2$—NH—;

Y is —CO—$R^1$—, —CO—$R^2$—S—, —CO—NH— or —$SO_2$—;

T is phenyl optionally substituted by halo, $C_1$-$C_4$-alkyl, $C_1$-$C_4$-alkoxy or cyano, or T is a heterocyclic group having 5 to 10 ring atoms wherein at least one of those ring atoms is a nitrogen, oxygen or sulphur atom, said heterocyclic group being optionally substituted by $C_1$-$C_4$-alkyl optionally substituted by $R^3$, $C_1$-$C_4$-alkoxy, phenyl or by a 5- or 6-membered heterocyclic ring having at least one ring nitrogen or oxygen atom;

$R^1$ and $R^2$ are each a bond or $C_1$-$C_4$-alkylene; and $R^3$ is phenyl or a 5- or 6-membered heterocyclic ring having at least one ring nitrogen atom.

Many of the compounds represented by formula I are capable of forming acid addition salts, particularly pharmaceutically acceptable acid addition salts. Pharmaceutically acceptable acid addition salts of the compound of formula I include those of inorganic acids, for example, hydrohalic acids such as hydrofluoric acid, hydrochloric acid, hydrobromic acid or hydroiodic acid, nitric acid, sulfuric acid, phosphoric acid; and organic acids, for example aliphatic monocarboxylic acids such as formic acid, acetic acid, trifluoroacetic acid, propionic acid and butyric acid, aliphatic hydroxy acids such as lactic acid, citric acid, tartaric acid or malic acid, dicarboxylic acids such as maleic acid or succinic acid, aromatic carboxylic acids such as benzoic acid, p-chlorobenzoic acid, diphenylacetic acid or triphenylacetic acid, aromatic hydroxy acids such as o-hydroxybenzoic acid, p-hydroxy-benzoic acid, 1-hydroxynaphthalene-2-carboxylic acid or 3-hydroxynaphthalene-2-carboxylic acid, and sulfonic acids such as methanesulfonic acid or benzenesulfonic acid. These salts may be prepared from compounds of formula I by known salt-forming procedures.

In those compounds where there is an asymmetric carbon atom the compounds exist in individual optically active isomeric forms or as mixtures thereof, e.g. as racemic or diastereomeric mixtures. The present invention embraces both individual optically active R and S isomers as well as mixtures, e.g. racemic or diastereomeric mixtures, thereof. Specific especially preferred compounds of the invention are those described hereinafter in the Examples.

The invention also provides a process for the preparation of compounds of formula I which comprises the steps of:

(i) (A) for the preparation of compounds of formula I where Y is —CO—R$^1$—, reacting a compound of formula II

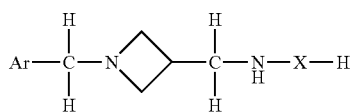

II wherein Ar and X are as hereinbefore defined, with a compound of formula III

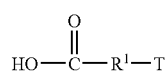

III or an amide-forming derivative thereof, wherein T and R$^1$ are as hereinbefore defined;

(B) for the preparation of compounds of formula I where Y is —CO—R$^2$—S—, reacting a compound of formula II wherein Ar and X are as hereinbefore defined, with a compound of formula IV

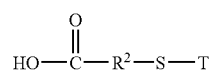

IV or an amide-forming derivative thereof, wherein R$^2$ and T are as hereinbefore defined; or (C) for the preparation of compounds of formula I where Y is —CO—NH—, reacting a compound of formula II wherein Ar and X are as hereinbefore defined, with a compound of formula V

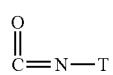

V wherein T is as hereinbefore defined; or (D) for the preparation of compounds of formula I where Y is —SO$_2$—, reacting a compound of formula II wherein Ar and X are as hereinbefore defined, with a compound of formula VI

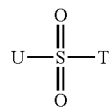

VI wherein T is as hereinbefore defined and U is halo; and (ii) recovering the product in free or salt form.

Process variant (A) may be carried out using known procedures for reacting amines with carboxylic acids (or amide-forming derivatives thereof such as acid halide derivatives), or analogously e.g. as hereinafter described in the Examples. The reaction is conveniently carried out with the carboxylic acid using an organic solvent, for example dimethylformamide (DMF), in the presence of one or more coupling agents, for example O-(7-azabenzo-triazol-1-yl)-1,1,3-,3-tetramethyluronium hexafluoro-phosphate (HATU), and a base, for example triethylamine (Et$_3$N). Suitable reaction temperatures are from 0° C. to 40° C., for example room temperature.

Process variant (B) may be carried out using known procedures for reacting amines with carboxylic acids (or amide-forming derivatives thereof such as acid halide derivatives), or analogously e.g. as hereinafter described in the Examples. The reaction is conveniently carried out with the carboxylic acid using an organic solvent, for example dichloromethane (DCM), in the presence of one or more coupling agents, for example [(benzotriazol-1-yloxy)-dimethylamino-methylene]-dimethyl-ammonium-tetrafluoro borate (TBTU) and a base, for example triethylamine. Suitable reaction temperatures are from 0° C. to 40° C., for example room temperature.

Process variant (C) may be carried out using known procedures for reacting amines with isocyanates, or analogously e.g. as hereinafter described in the Examples. The reaction is conveniently carried out using an organic solvent, for example dimethylformamide. Suitable reaction temperatures are from 10° C. to 40° C., for example room temperature.

Process variant (D) may be carried out using known procedures for reacting amines with sulfonyl halides, or analogously e.g. as hereinafter described in the Examples. The reaction is conveniently carried out using an organic solvent, for example dimethylformamide, in the presence of a base, for example triethylamine. Suitable reaction temperatures are from 10° C. to 40° C., for example room temperature.

Compounds of formula II where X is a bond may be prepared by reducing a compound of formula VII

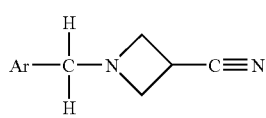

VII where Ar is as hereinbefore defined. The reaction may be effected using known methods for reducing nitriles to amines, or analogously e.g. as hereinafter described in the Examples. The reaction is conveniently carried out using a reducing agent such as lithium aluminium hydride (LiAlH$_4$) and an organic solvent such as tetrahydrofuran (THF). Suitable reaction temperatures are from 10° C. to 40° C., for example room temperature.

Compounds of formula II where X is —CO—CH$_2$—NH— are novel and may be prepared by reacting a compound of formula II where X is a bond with a suitable amide bonding forming agent, e.g. HATU or TBTU, and a protected glycine, e.g. t-butyloxycarbonyl-glycine (BOC glycine). The reaction may be effected using known methods for inserting glycine spacers into amines, or analogously e.g. as hereinafter described in the Examples. The protecting group may be removed using a strong acid for example trifluoroacetic acid. Suitable reaction temperatures are from 10° C. to 40° C., for example room temperature.

Compounds of formula III are either commercially available or may be prepared by using known procedures for preparing carboxylic acids.

Compounds of formula IV are either commercially available or may be prepared by using known procedures for preparing carboxylic acids that contain a sulfanyl group. Compounds of formula V are either commercially available or may be prepared by using known procedures for preparing isocyanates.

Compounds of formula VI are either commercially available or may be prepared by using known procedures for preparing sulfonyl chlorides.

Compounds of formula VII may be prepared by reacting a compound of formula VIII

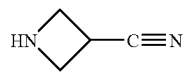

VIII with a compound of formula IX

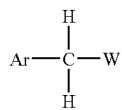

IX where Ar is as hereinbefore defined and W is halo, for example bromo. The reaction may be effected using known methods for reacting amines with alkyl halides, or analogously e.g. as hereinafter described in the Examples. The reaction is conveniently carried out using an organic solvent, for example dichloromethane, in the presence of a base, for example triethylamine. Suitable reaction temperatures are from 10° C. to 40° C., for example room temperature The compound of formula VIII, which is azetidine-3-carbonitrile, may be prepared by reacting 1-benzhydryl-azetidine-3-carbonitrile with 1-chloroethylchloroformate as hereinafter described in the Example 1. The reaction may be effected using known methods for reacting azetidines with haloesters. It is conveniently carried out using an organic solvent, for example dichloromethane.

Compounds of formula IX are either commercially available or may be prepared by using known procedures for preparing substituted alkyl halides.

Compounds of formula I in free form may be converted into salt form, and vice versa, in a conventional manner. The compounds in free or salt form can be obtained in the form of hydrates or solvates containing a solvent used for crystallisation. Compounds of formula I can be recovered from reaction mixtures and purified in a conventional manner. Isomers, such as enantiomers, may be obtained in a conventional manner, e.g. by fractional crystallisation or asymmetric synthesis from correspondingly asymmetrically substituted, e.g. optically active, starting materials.

Compounds of formula I and their pharmaceutically acceptable salts are useful as pharmaceuticals. In particular, they inhibit human chemokine receptor CCR-3. The effect of compounds of the formula I, i.e. agents of the invention, on the binding of human eotaxin to human CCR-3 is determined by the following assay:

Recombinant cells expressing human CCR-3 are captured by wheatgerm agglutinin (WGA) polyvinyltoluidene (PVT) SPA beads (available from Marshal), through a specific interaction between the WGA and carbohydrate residues of glycoproteins on the surface of the cells. [$^{125}$I]-human eotaxin (available from Amersham) binds specifically to CCR-3 receptors bringing the [$^{125}$I]-human eotaxin in close proximity to the SPA beads. Emitted â-particles from the [$^{125}$I]-human eotaxin excite, by its proximity, the fluorophore in the beads and produce light. Free [$^{125}$I]-human eotaxin in solution is not in close proximity to the scintillant and hence does not produce light. The scintillation count is therefore a measure of the extent to which the test compound inhibits binding of the eotaxin to the CCR-3.

Preparation of Assay Buffer: 5.96 g HEPES and 7.0 g sodium chloride are dissolved in distilled water and 1 M aqueous $CaCl_2$ (1 ml) and 1M aqueous $MgCl_2$ (5 ml) are added. The pH is adjusted to 7.6 with NaOH and the solution made to a final volume of 1 l using distilled water. 5 g bovine serum albumin and 0.1 g sodium azide are then dissolved in the solution and the resulting buffer stored at 4° C. A COMPLETE™ protease inhibitor cocktail tablet (available from Boehringer) is added per 50 ml of the buffer on the day of use.

Preparation of Homogenisation Buffer: Tris-base (2.42 g) is dissolved in distilled water, the pH of the solution is adjusted to 7.6 with hydrochloric acid and the solution is diluted with distilled water to a final volume of 1 l. The resulting buffer is stored at 4° C. A COMPLETE™ protease inhibitor cocktail tablet is added per 50 ml of the buffer on the day of use.

Preparation of membranes: Confluent rat basophil leukaemia (RBL-2H3) cells stably expressing CCR3 are removed from tissue culture flasks using enzyme-free cell dissociation buffer and resuspended in phosphate-buffered saline. The cells are centrifuged (800 g, 5 minutes), the pellet resuspended in ice-cold homogenisation buffer using 1 ml homogenisation buffer per gram of cells and incubated on ice for 30 minutes. The cells are homogenised on ice with 10 strokes in a glass mortar and pestle. The homogenate is centrifuged (800 g, 5 minutes, 4° C.), the supernatant further centrifuged (48,000 g, 30 minutes, 4° C.) and the pellet redissolved in Homogenisation Buffer containing 10% (v/v) glycerol. The protein content of the membrane preparation is estimated by the method of Bradford (Anal. Biochem. (1976) 72:248) and aliquots are snap frozen and stored at −80° C.

The assay is performed in a final volume of 250 µl per well of an OPTIPLATE™ microplate (ex Canberra Packard). To selected wells of the microplate are added 50 µl of solutions of a test compound in Assay Buffer containing 5% DMSO (concentrations from 0.01 nM to 10 µM). To determine total binding, 50 µl of the Assay Buffer containing 5% DMSO is added to other selected wells. To determine non-specific binding, 50 µl of 100 nM human eotaxin (ex R&D Systems) in Assay Buffer containing 5% DMSO is added to further selected wells. To all wells are added 50 µl [$^{125}$I]-Human eotaxin (ex Amersham) in Assay Buffer containing 5% DMSO at a concentration of 250 pM (to give a final concentration of 50 pM per well), 50 µL of WGA-PVT SPA beads in Assay Buffer (to give a final concentration of 1.0 mg beads per well) and 100 µl of the membrane preparation at a concentration of 100 µg protein in Assay Buffer (to give a final concentration of 10 μg protein per well). The plate is then incubated for 4 hours at room temperature. The plate is sealed using TOPSEAL-S™ (ex Canberra Packard) according to the manufacturer's instructions. The resulting scintillations are counted using a Canberra Packard TopCount, each well being counted for 1 minute. The concentration of test compound at which 50% inhibition occurs ($IC_{50}$) is determined from concentration-inhibition curves in a conventional manner.

The compounds of the Examples hereinbelow have $IC_{50}$ values of the order of 1 μM or less in the above assay. For instance, the compounds of Examples 5, 7 and 8 have $IC_{50}$ values of 0.297, 0.420 and 0.198 μM respectively.

Having regard to their inhibition of binding of CCR-3, agents of the invention are useful in the treatment of conditions mediated by CCR-3, particularly inflammatory or allergic conditions. Treatment in accordance with the invention may be symptomatic or prophylactic.

Accordingly, agents of the invention are useful in the treatment of inflammatory or obstructive airways diseases, resulting, for example, in reduction of tissue damage, bronchial hyperreactivity, remodelling or disease progression. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, i.e. therapy for or intended to restrict or abort symptomatic attack when it occurs, e.g. anti-inflammatory (e.g. corticosteroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant form any previously administered symptomatic asthma therapy.

Other inflammatory or obstructive airways diseases and conditions to which the present invention is applicable include acute lung injury (ALI), acute/adult respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

Having regard to their anti-inflammatory activity, in particular in relation to inhibition of eosinophil activation, agents of the invention are also useful in the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Löffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

Agents of the invention are also useful in the treatment of inflammatory or allergic conditions of the skin, for example psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, and other inflammatory or allergic conditions of the skin.

Agents of the invention may also be used for the treatment of other diseases or conditions, in particular diseases or conditions having an inflammatory component, for example, treatment of diseases and conditions of the eye such as conjunctivitis, keratoconjunctivitis sicca, and vernal conjunctivitis, diseases affecting the nose including allergic rhinitis, and inflammatory conditions of the gastrointestinal tract, for example inflammatory bowel disease such as ulcerative colitis and Crohn's disease.

The effectiveness of an agent of the invention in inhibiting inflammatory conditions, for example in inflammatory airways diseases, may be demonstrated in an animal model, e.g. a mouse or rat model, of airways inflammation or other inflammatory conditions, for example as described by Szarka et al, *J. Immunol. Methods* (1997) 202:49-57; Renzi et al, *Am. Rev. Respir. Dis.* (1993) 148:932-939; Tsuyuki et al., *J. Clin. Invest.* (1995) 96:2924-2931; and Cernadas et al (1999) *Am. J. Respir. Cell Mol. Biol.* 20:1-8.

The agents of the invention are also useful as co-therapeutic agents for use in combination with other drug substances such as anti-inflammatory, bronchodilatory, antihistamine or anti-tussive drug substances, particularly in the treatment of obstructive or inflammatory airways diseases such as those mentioned hereinbefore, for example as potentiators of therapeutic activity of such drugs or as a means of reducing required dosaging or potential side effects of such drugs. An agent of the invention may be mixed with the other drug substance in a fixed pharmaceutical composition or it may be administered separately, before, simultaneously with or after the other drug substance.

Such anti-inflammatory drugs steroids, in particular glucocorticosteroids such as budesonide, beclamethasone dipropionate, fluticasone propionate, ciclesonide or mometasone furoate, or steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/35668, WO 03/48181, WO 03/62259, WO 03/64445, WO 03/72592, WO 04/39827 and WO 04/66920; non-steroidal glucocorticoid receptor agonists, such as those described in DE 10261874, WO 00/00531, WO 02/10143, WO 03/82280, WO 03/82787, WO 03/86294, WO 03/104195, WO 03/101932, WO 04/05229, WO 04/18429, WO 04/19935 and WO 04/26248; LTB4 antagonists such as BIIL 284, CP-195543, DPC$_{11870}$, LTB4 ethanolamide, LY 293111, LY 255283, CGS025019C, CP-195543, ONO-4057, SB 209247, SC-53228 and those described in U.S. Pat. No. 5,451,700; LTD4 antagonists such include montelukast, pranlukast, zafirlukast, accolate, SR2640, Wy-48,252, ICI 198615, MK-571, LY-171883, Ro 24-5913 and L-648051; dopamine receptor agonists such as cabergoline, bromocriptine, ropinirole and 4-hydroxy-7-[2-[[2-[[3-(2-phenylethoxy)propyl]sulfonyl]ethyl]-amino] ethyl]-2(3H)-benzothiazolone and pharmaceutically acceptable salts thereof (the hydrochloride being Viozan®—AstraZeneca); PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID(TM) CC-10004 (Celgene), VM554/UM565 (Vernalis), T-440 (Tanabe), KW-4490 (Kyowa Hakko Kogyo), and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607 and WO 04/037805; A2a agonists such as those described in EP 409595A2, EP 1052264, EP 1241176, WO 94/17090, WO 96/02543, WO 96/02553, WO 98/28319, WO 99/24449, WO 99/24450, WO 99/24451, WO 99/38877, WO 99/41267, WO 99/67263, WO 99/67264, WO 99/67265, WO 99/67266, WO 00/23457, WO 00/77018, WO 00/78774, WO 01/23399, WO 01/27130, WO 01/27131, WO 01/60835, WO 01/94368, WO 02/00676, WO 02/22630, WO 02/96462, WO 03/086408, WO 04/039762, WO 04/039766, WO 04/045618, WO 04/046083; and A2b antagonists such as those described in WO 02/42298. Such bronchodilatory drugs include anticholinergic or antimuscarinic agents, in particular ipratropium bromide, oxitropium bromide, tiotropium salts and CHF 4226 (Chiesi), and glycopyrrolate, but also those described in EP 424021, U.S. Pat. No. 3,714,357, U.S. Pat. No. 5,171,744, WO 01/04118, WO 02/00652, WO 02/51841, WO 02/53564, WO 03/00840, WO 03/33495, WO 03/53966, WO 03/87094, WO 04/018422 and WO 04/05285; and beta (β)-2-adrenoceptor agonists such as beta-2 adrenoceptor agonists such as albuterol (salbutamol), metaproterenol, terbutaline, salmeterol fenoterol, procaterol, and especially, formoterol, carmoterol and pharmaceutically acceptable salts thereof, and compounds (in free or salt or solvate form) of formula I of WO 0075114, which document is incorporated herein by reference, preferably compounds of the Examples thereof, especially a compound of formula

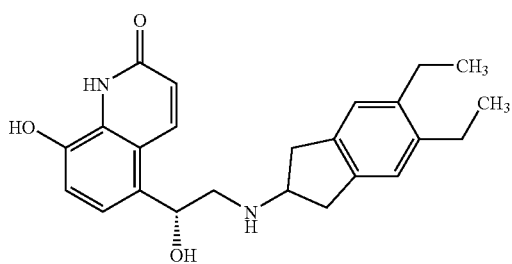

and pharmaceutically acceptable salts thereof, as well as compounds (in free or salt or solvate form) of formula I of WO 04/16601, and also compounds of EP 1440966, JP 05025045, WO 93/18007, WO 99/64035, US 2002/0055651, WO 01/42193, WO 01/83462, WO 02/66422, WO 02/70490, WO 02/76933, WO 03/24439, WO 03/42160, WO 03/42164, WO 02/72539, WO 03/91204, WO 03/99764, WO 04/16578, WO 04/22547, WO 04/32921, WO 04/33412, WO 04/37768, WO 04/37773, WO 04/37807, WO 04/39762, WO 04/39766, WO 04/45618 WO 04/46083, WO 04/80964, EP1460064, WO 04/087142, WO 04/089892, EP 01477167, US 2004/0242622, US 2004/0229904, WO 04/108675, WO 04/108676, WO 05/033121, WO 05/040103 and WO 05/044787.

Co-therapeutic antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine as well as those disclosed in WO 03/099807, WO 04/026841, JP 2004107299.

Combinations of agents of the invention and one or more steroids, beta-2 agonists, PDE4 inhibitors or LTD4 antagonists may be used, for example, in the treatment of COPD or, particularly, asthma. Combinations of agents of the invention and anticholinergic or antimuscarinic agents, PDE4 inhibitors, dopamine receptor agonists or LTB4 antagonists may be used, for example, in the treatment of asthma or, particularly, COPD.

Other useful combinations of agents of the invention with anti-inflammatory drugs are those with other antagonists of chemokine receptors, e.g. CCR-1, CCR-2, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, Takeda antagonists such as N-[[4-[[[6,7-dihydro-2-(4-methylphenyl)-5H-benzocyclohepten-8-yl]carbonyl]amino]phenyl]-methyl]tetrahydro-N,N-dimethyl-2H-pyran-4-aminium chloride (TAK-770), CCR-5 antagonists described in U.S. Pat. No. 6,166,037 (particularly claims 18 and 19), WO 00/66558 (particularly claim 8), and WO 00/66559 (particularly claim 9), WO 04/018425 and WO 04/026873.

In accordance with the foregoing, the invention also provides a method for the treatment of a condition mediated by CCR-3, for example an inflammatory or allergic condition, particularly an inflammatory or obstructive airways disease, which comprises administering to a subject, particularly a human subject, in need thereof an effective amount of a compound of formula I in a free or pharmaceutically acceptable salt form as hereinbefore described. In another aspect the invention provides the use of a compound of formula I, in free or pharmaceutically acceptable salt form, as hereinbefore described for the manufacture of a medicament for the treatment of a condition mediated by CCR-3, e.g. an inflammatory or allergic condition, particularly an inflammatory or obstructive airways disease.

The agents of the invention may be administered by any appropriate route, e.g. orally, for example in the form of a tablet or capsule; parenterally, for example intravenously; by inhalation, for example in the treatment of inflammatory or obstructive airways disease; intranasally, for example in the treatment of allergic rhinitis; topically to the skin, for example in the treatment of atopic dermatitis; or rectally, for example in the treatment of inflammatory bowel disease.

In a further aspect, the invention also provides a pharmaceutical composition comprising as active ingredient a compound of formula I in free or pharmaceutically acceptable salt form, optionally together with a pharmaceutically acceptable diluent or carrier therefor. The composition may contain a co-therapeutic agent such as an anti-inflammatory or bronchodilatory drug as hereinbefore described. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g. patches. Compositions for inhalation may comprise aerosol or other atomizable or dry powder formulations.

When the composition comprises an aerosol formulation, it preferably contains, for example, a hydro-fluoro-alkane (HFA) propellant such as HFA134a or HFA227 or a mixture of these, and may contain one or more co-solvents known in the art such as ethanol (up to 20% by weight), and/or one or more surfactants such as oleic acid or sorbitan trioleate, and/or one or more bulking agents such as lactose. When the composition comprises a dry powder formulation, it preferably contains, for example, the compound of formula I having a particle diameter up to 10 microns, optionally together with a diluent or carrier, such as lactose, of the desired particle size distribution and a compound that helps to protect against product performance deterioration due to moisture e.g. magnesium stearate. When the composition comprises a nebulised formulation, it preferably contains, for example, the compound of formula I either dissolved, or suspended, in a vehicle containing water, a co-solvent such as ethanol or propylene glycol and a stabiliser, which may be a surfactant.

The invention includes (A) an agent of the invention in inhalable form, e.g. in an aerosol or other atomizable composition or in inhalable particulate, e.g. micronised form, (B) an inhalable medicament comprising an agent of the invention in inhalable form; (C) a pharmaceutical product comprising such an agent of the invention in inhalable form in association with an inhalation device; and (D) an inhalation device containing an agent of the invention in inhalable form.

Dosages of agents of the invention employed in practising the present invention will of course vary depending, for example, on the particular condition to be treated, the effect desired and the mode of administration. In general, suitable daily dosages for administration by inhalation are of the order of 0.01 to 30 mg/kg while for oral administration suitable daily doses are of the order of 0.01 to 100 mg/kg.

The invention is illustrated by the following Examples.

EXAMPLES

Compounds of formula I, which are also compounds of formula X

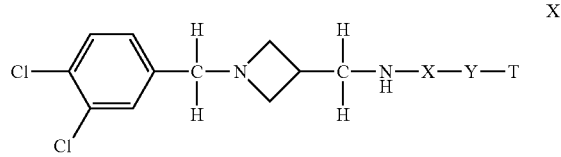

are shown in the following table, the method of preparation being described hereinafter. The table also shows characterising mass spectrometry data ([MH]+) and, where the Example is a salt, the identity of the salt-forming acid.

TABLE I

| Ex. | X | Y | T | M/S |
|---|---|---|---|---|
| 1 | 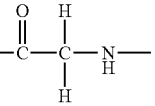 |  | 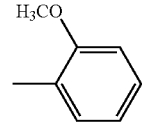 | — |
| 2 | 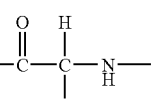 | 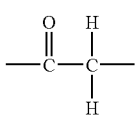 | 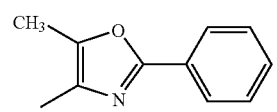 | 502.07 |
| 3 | 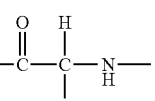 |  | 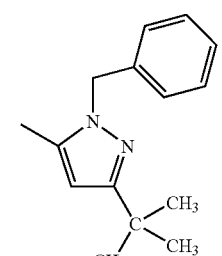 | 543.22 |
| 4 |  |  | 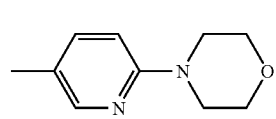 | 493.06 |

TABLE I-continued

| Ex. | X | Y | T | M/S |
|---|---|---|---|---|
| 5 | —C(=O)—CH(H)—N(H)— | —C(=O)— | 4-chlorophenyl | — |
| 6 | —C(=O)—CH(H)—N(H)— | —C(=O)— | 3-methylphenyl | — |
| 7 | —C(=O)—CH(H)—N(H)— | —C(=O)— | 2,5-dimethyl-1-(pyridin-4-ylmethyl)-1H-pyrrol-3-yl | 515.13 |
| 8 | — | —C(=O)—CH(H)—S— | 2-methyl-benzothiazol-6-yl-O—CH$_2$—CH$_3$ (6-ethoxy-2-methylbenzothiazol-yl) | 495.8 |
| 9 | —C(=O)—CH(H)—N(H)— | —C(=O)—N(H)— | 3-chlorophenyl | — |
| 10 | — | —C(=O)—N(H)— | 4-cyanophenyl | — |
| 11 | —C(=O)—CH(H)—N(H)— | —S(=O)$_2$— | 4-methoxyphenyl | — |

Preparation of Starting Materials 1-(3,4-Dichloro-benzyl)-azetidine-3-carbonitrile A solution of 1-Benzhydryl-azetidine-3-carbonitrile (0.25 g, 1.0 mmol) in dichloromethane (2 ml) is treated with 1-chloroethylchloroformate (0.12 ml, 1.1 mmol). The reaction mixture is stirred at room temperature for 3 hours, the solvent evaporated and the residue taken-up in methanol and refluxed for 1 hour. The reaction mixture is cooled to room temperature and stirred for a further 18 hours. The solvent is evaporated to afford crude azetidine-3-carbonitrile hydrochloride. The crude azetidine-3-carbonitrile is dissolved in dichloromethane (3 ml) and treated with triethylamine (0.25 ml, 2.0 mmol) and 3,4-dichlorobenzylbromide (0.24 g, 1.0 mmol). The reaction mixture is stirred at ambient temperature for 2 hours, then washed with water, the organic phase dried over magnesium sulphate and evaporated. The crude product is purified by chromatography over flash silica using hexane:ethylacetate 2:1 as eluent to afford 1-(3,4-Dichloro-benzyl)-azetidine-3-carbonitrile. [MH]+ 240.97

C-[1-(3,4-Dichloro-benzyl)-azetidin-3-yl]-methylamine

A solution of 1-(3,4-Dichloro-benzyl)-azetidine-3-carbonitrile (0.083 g, 0.347 mmol) in dry THF (2 ml) cooled to 0° C. is treated with a 1.0 M solution of lithium aluminium hydride in THF (0.347 ml). The reaction mixture is allowed to warm to ambient temperature and stirred for a one hour. The reaction mixture is quenched with saturated sodium sulphate solution and filtered. The filtrate is evaporated to afford the title compound. [MH] 244.97.

({[1-(3,4-Dichloro-benzyl)-azetidin-3-ylmethyl]-carbamoyl}-methyl)-carbamic acid tert-butyl ester A solution of tert-Butoxycarbonylamino-acetic acid (1.88 g, 10.7 mmol) in dichloromethane (15 ml) is treated with triethylamine (1.5 ml, 10.7 mmol) and [Dimethylamino-[1,2,3]-triazolo-[4,5-b]pyridin-3-yloxy)-methylene]-dimethyl-ammonium hexafluoro phosphate (4.06 g, 10.7 mmol) and stirred for 5 minutes. To the reaction mixture is added a solution of C-[1-(3,4-Dichloro-benzyl)-azetidin-3-yl]-methylamine (2.64 g, 10.7 mmol) in dichloromethane (15 ml)

with stirring for a further 3 hours. The reaction mixture is partitioned between dichloromethane and saturated sodium bicarbonate solution, the organic phase is washed with brine, dried over magnesium sulphate and evaporated. The crude product is purified by chromatography over flash silica eluting with 7% methanol in dichloromethane to afford the title compound.

2-Amino-N-[1-(3,4-dichloro-benzyl)-azetidin-3-ylmethyl]-acetamide

A solution of ({[1-(3,4-Dichloro-benzyl)-azetidin-3-ylmethyl]-carbamoyl}-methyl)-carbamic acid tert-butyl ester (0.082 g, 0.203 mmol) in a 2:1 mixture of dichloromethane: trifluoroacetic acid (1.5 ml) is stirred at ambient temperature for 3.5 hours, then evaporated to dryness to afford the trifluoroacetate salt of the titled product. This material is dissolved in methanol and stirred with Amberlyst A21™ ion exchange resin for 6 hours. The resin is removed by filtration to afford the title product.

Example 1

N-({[1-(3,4-Dichloro-benzyl)-azetidin-3-ylmethyl]-carbamoyl}-methyl)-2-methoxy-benzamide A solution of 2-methoxybenzoic acid in dimethylformamide is treated with triethylamine (2 M equivalents) and [dimethylamino-([1,2,3]triazolo[4,5-b]pyridin-3-yloxy)-methylene]-dimethyl-ammonium hexafluoro phosphate (1 M equivalent). To the reaction mixture is added a solution of 2-Amino-N-[1-(3,4-dichloro-benzyl)-azetidin-3-ylmethyl]-acetamide (1 M equivalent) in dimethylformamide and left to stir for 1.5 hours. The reaction mixture is diluted with chloroform/methanol 50:50 and applied to a SCX-3 1 g cartridge. The cartridge is washed with chloroform/methanol 50:50, and the compound eluted with a solution of 10% ammonia in methanol. The solvent is evaporated to afford the title compound.

The compounds of Examples 2 to 7 are made using procedures that are analogous to those described in Example 1.

Example 8

N-[1-(3,4-Dichloro-benzyl)-azetidin-3-yl-methyl]-2-(6-ethoxy-benzothiazol-2-ylsulfanyl)-acetamide A solution of (6-Ethoxy-benzothiazol-2-ylsulfanyl)-acetic acid (0.087 g, 0.326 mmol) in dichloromethane (3 ml) is treated with triethylamine (0.041 ml, 0.326 mmol) and [(Benzotriazol-1-yloxy)-dimethylamino-methylene]-dimethyl-ammonium; tetrafluoro borate (0.104 g, 0.326 mmol) and stirred at ambient temperature for 3 minutes. To the reaction mixture is added a solution of C-[1-(3,4-Dichloro-benzyl)-azetidin-3-yl]-methylamine (0.08 g, 3.26 mmol) in dichloromethane (1 ml), with stirred for a further 3 hours. The reaction mixture is partitioned between ethyl acetate and sodium bicarbonate solution. The organic phase is dried over magnesium sulphate and evaporated. The crude product is purified by flash silica chromatography using 95:5 dichloromethane:methanol as eluent to afford N-[1-(3,4-Dichloro-benzyl)-azetidin-3-ylmethyl]-2-(6-ethoxy-benzothiazol-2-ylsulfanyl)-acetamide. [MH]+ 495.8.

Example 9

2-[3-(3-Chloro-phenyl)-ureido]-N-[1-(3,4-dichloro-benzyl)-azetidin-3-ylmethyl]-acetamide]

A solution of 2-Amino-N-[1-(3,4-dichloro-benzyl)-azetidin-3-ylmethyl]-acetamide (1 M equivalent) in dimethylformamide is treated with a solution of the isocyanate (1.5 M equivalents) in dimethylformamide and left at room temperature overnight. The reaction mixture is diluted with chloroform/methanol 50:50 and applied to a SCX-3 1 g cartridge. The cartridge is washed with chloroform methanol 50:50, and the compound eluted with a solution of 10% ammonia in methanol. The solvent is evaporated to afford the title compound.

The compound of Example 10 is made using procedures that are analogous to those described in Example 9.

Example 11

N-[1-(3,4-Dichloro-benzyl)-azetidin-3-ylmethyl]-2-(4-methoxy-benzenesulfonylamino)-acetamide A solution of 2-Amino-N-[1-(3,4-dichloro-benzyl)-azetidin-3-ylmethyl]-acetamide (1 M equivalent) in dimethylformamide is treated with a solution triethylamine (3 M equivalents) followed by a solution of the sulphonyl chloride (1.5 M equivalents) in dimethylformamide and left at ambient temperature overnight. The reaction mixture is diluted with chloroform/methanol 50:50 and applied to a SCX-3 1 g cartridge. The cartridge is washed with chloroform methanol 50:50, and the compound eluted with a solution of 10% ammonia in methanol. The solvent is evaporated to afford the title compound.

The invention claimed is:
1. A compound of formula I

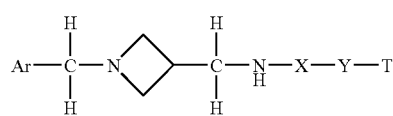

in free or salt form, wherein
Ar is phenyl optionally substituted by halo, $C_1$-$C_8$-alkyl, $C_1$-$C_8$-alkoxy, cyano, nitro, —$SO_2$—$C_1$-$C_8$-alkyl, —$SO_2$—NH—$C_1$-$C_8$-alkyl or —$SO_2$—N—($C_1$-$C_8$-alkyl)$_2$;
X is —CO—$CH_2$—NH—;
Y is —CO—$R^1$—, —CO—$R^2$—S—, —CO—NH— or —$SO_2$—;
T is phenyl optionally substituted by halo, $C_1$-$C_8$-alkyl, $C_1$-$C_8$-alkoxy or cyano, or T is a heterocyclic group selected from the group consisting of oxazolyl, pyrazolyl, pyridyl, and benzothiazol,
said heterocyclic group being optionally substituted by halo, $C_1$-$C_8$-alkyl optionally substituted by $R^3$, $C_1$-$C_8$-alkoxy optionally substituted by $R^3$, phenyl or by a 5- or 6-membered heterocyclic ring having at least one ring nitrogen, oxygen or sulphur atom;
$R^1$ and $R^2$ are each a bond or $C_1$-$C_8$-alkylene; and
$R^3$ is phenyl or a 5- or 6-membered heterocyclic ring having at least one ring nitrogen, oxygen or sulphur atom.

2. A compound according to claim 1, wherein

Ar is phenyl optionally substituted by halo;

X is —CO—CH$_2$—NH—;

Y is —CO—R$^1$—, —CO—R$^2$—S—, —CO—NH— or —SO$_2$—;

T is phenyl optionally substituted by halo, C$_1$-C$_8$-alkyl, C$_1$-C$_8$-alkoxy or cyano, or T is a heterocyclic group selected from the group consisting of oxazolyl, pyrazolyl, pyridyl, and benzothiazol, said heterocyclic group being optionally substituted by C$_1$-C$_8$-alkyl optionally substituted by R$^3$, C$_1$-C$_8$-alkoxy, phenyl or by a 5- or 6-membered heterocyclic ring having at least one ring nitrogen, oxygen or sulphur atom;

R$^1$ and R$^2$ are each a bond or C$_1$-C$_8$-alkylene; and

R$^3$ is phenyl or a 5- or 6-membered heterocyclic ring having at least one ring nitrogen, oxygen or sulphur atom.

3. A compound according to claim 1, wherein

Ar is phenyl optionally substituted by halo;

X is —CO—CH$_2$—NH—;

Y is —CO—R$^1$—, —CO—R$^2$—S—, —CO—NH— or —SO$_2$—;

T is phenyl optionally substituted by halo, C$_1$-C$_4$-alkyl, C$_1$-C$_4$-alkoxy or cyano, or T is a heterocyclic group selected from pyrazolyl or benzothiazol, said heterocyclic group being optionally substituted by C$_1$-C$_4$-alkyl optionally substituted by R$^3$, C$_1$-C$_4$-alkoxy, phenyl or by a 5- or 6-membered heterocyclic ring having at least one ring nitrogen or oxygen atom;

R$^1$ and R$^2$ are each a bond or C$_1$-C$_4$-alkylene; and

R$^2$ is phenyl or a 5- or 6-membered heterocyclic ring having at least one ring nitrogen atom,

4. A compound according to claim 1, wherein X, Y, T, and Ar are as shown in the following table -continued

| X | Y | T | Ar |
|---|---|---|---|
| (−C(=O)−CH(H)−NH−) | (−C(=O)−) | (4-pyridylmethyl-N-(2,5-dimethyl-3-methylpyrrolyl)) | (3,4-dichlorophenyl) |
| (−C(=O)−CH(H)−NH−) | (−C(=O)−NH−) | (3-chlorophenyl) | (3,4-dichlorophenyl) |
| (−C(=O)−CH(H)−NH−) | (−S(=O)₂−) | (4-methoxyphenyl) | (3,4-dichlorophenyl) |

5. A compound according to claim 1 for use as a pharmaceutical.

6. A pharmaceutical composition comprising as active ingredient a compound according to claim 1, optionally together with a pharmaceutically acceptable diluent or carrier therefor.

* * * * *